United States Patent [19]
Dunkelman et al.

[11] Patent Number: 5,792,603
[45] Date of Patent: Aug. 11, 1998

[54] APPARATUS AND METHOD FOR STERILIZING, SEEDING, CULTURING, STORING, SHIPPING AND TESTING TISSUE, SYNTHETIC OR NATIVE, VASCULAR GRAFTS

[75] Inventors: Noushin Dunkelman, San Diego; Alvin E. Peterson, Jamul; Lee Kevin Landeen; Joan Zeltinger, both of San Diego, all of Calif.

[73] Assignee: Advanced Tissue Sciences, Inc., San Jose, Calif.

[21] Appl. No.: 672,697

[22] Filed: Jun. 27, 1996

Related U.S. Application Data

[63] Continuation-in-part of Ser. No. 430,768, Apr. 27, 1995.

[51] Int. Cl.[6] ............................................. C12M 3/00
[52] U.S. Cl. ........................... 435/1.2; 435/399; 435/401; 435/284.1; 435/286.5; 435/297.2; 600/36; 623/1
[58] Field of Search .................... 435/1.1, 284.1, 435/286.5, 286.6, 289.1, 293.1, 293.2, 297.2, 297.4, 301.1, 1.2, 395, 398, 399, 401, 402; 600/36; 623/1; 425/392

[56] References Cited

U.S. PATENT DOCUMENTS

| | | |
|---|---|---|
| 3,734,851 | 5/1973 | Matsumura . |
| 4,050,893 | 9/1977 | Hancock et al. ................. 8/94.11 |
| 4,417,861 | 11/1983 | Tolbert . |
| 4,639,422 | 1/1987 | Geimer et al. . |
| 4,911,713 | 3/1990 | Sauvage et al. ................. 623/1 |
| 4,988,623 | 1/1991 | Schwarz et al. . |
| 5,026,650 | 6/1991 | Schwarz et al. . |
| 5,043,260 | 8/1991 | Jauregui . |
| 5,081,035 | 1/1992 | Halberstadt et al. . |
| 5,153,131 | 10/1992 | Wolf et al. . |
| 5,153,132 | 10/1992 | Goodwin et al. . |
| 5,153,133 | 10/1992 | Schwarz et al. . |
| 5,155,034 | 10/1992 | Wolf et al. . |
| 5,155,035 | 10/1992 | Schwarz et al. . |
| 5,230,693 | 7/1993 | Williams et al. . |
| 5,266,480 | 11/1993 | Naughton et al. . |
| 5,308,764 | 5/1994 | Goodwin et al. . |
| 5,376,110 | 12/1994 | Tu et al. ........................... 623/1 |

FOREIGN PATENT DOCUMENTS

| | | |
|---|---|---|
| WO 90/13639 | 11/1990 | WIPO . |
| WO 92/11355 | 7/1992 | WIPO . |
| WO 93/01843 | 2/1993 | WIPO . |
| WO 93/12805 | 7/1993 | WIPO . |
| WO 93/18132 | 9/1993 | WIPO . |
| WO 94/25584 | 11/1994 | WIPO . |

OTHER PUBLICATIONS

Eskin et al. "Behavior of Endothelial Cells Cultured on Silastic and Dacron Velour Under Flow Conditions In Vitro:." Artificial Organs. vol. 7, No. 1 (1983), pp. 31–37.
Van Wachem et al. "Vacuum cell seeding:." Biomaterials, vol. 11 (Oct. 1990), pp. 602–606.
Atkinson, et al., *Biochemical Engineering And Biotechnology Handbook*; pp. 476–487 (1991).
Halberstadt, et al., "The In Vitro Growth of a Three–Dimensional Human Dermal Replacement Using a Single–Pass Perfusion System," *Biotechnology and Bioengineering* 43:740–746 (1994).

*Primary Examiner*—William H. Beisner
*Attorney, Agent, or Firm*—Pennie & Edmonds LLP

[57] ABSTRACT

An apparatus and method for sterilizing, seeding, culturing, storing, shipping, and testing vascular grafts is disclosed. Specifically, the present invention relates to an apparatus and method for seeding and culturing vascular grafts with human cells. The apparatus includes a fluid reservoir, a pump, an alternating pressure source, and at least one treatment chamber. By alternating pressure to a support structure within the treatment chamber upon which a vascular graft scaffold is positioned, a varying radial stress is placed on the scaffold. In an alternative embodiment, fluid is pumped directly through the vascular graft subjecting the vascular graft to radial and shear stresses. Applying shear and/or radial stresses to the vascular graft during seeding and culturing simulates physiological conditions.

67 Claims, 6 Drawing Sheets

APPARATUS AND METHOD FOR STERILIZING, SEEDING, CULTURING, STORING, SHIPPING AND TESTING TISSUE, SYNTHETIC OR NATIVE, VASCULAR GRAFTS

RELATED APPLICATIONS

This application is a continuation in part of co-pending application Ser. No. 08/430,768, filed Apr. 27, 1995.

BACKGROUND OF THE INVENTION

1. Technical Field

The present invention relates to the sterilization, seeding, culturing, storing, shipping, and testing of vascular grafts. Specifically, the present invention relates to an apparatus and method for sterilizing vascular grafts and then seeding and culturing the grafts with human cells, resulting in grafts populated with viable human cells.

2. Discussion of the Related Art

Vascular and thoracic surgeons use vascular grafts to repair or replace segments of arterial and venous blood vessels that are weakened, damaged, or obstructed due to trauma or disease such as aneurysm, atherosclerosis, and diabetes mellitus. Historically, vascular grafts have been either homografts, such as the patient's own saphenous vein or internal mammary artery, prosthetic grafts made of synthetic materials such as polyester (e.g., Dacron), expanded polytetraflouroethylene (ePTFE), and other composite materials, or fresh or fixed biological tissue grafts.

However, synthetic grafts generally have inadequate patency rates for many uses, while the harvesting of homografts requires extensive surgery which is time-consuming, costly, and traumatic to the patient. Fixed tissue grafts do not allow for infiltration and colonization by the host cells, which is essential to remodeling and tissue maintenance. Consequently, fixed tissue grafts degrade with time and will eventually malfunction.

Due to the inadequacies of these currently available synthetic and biological grafts, and the high cost and limited supply of homografts, tissue engineered grafts are being developed which are sterilized, then seeded and cultured, in vitro, with cells. These tissue engineered grafts may be superior to other grafts for use in replacement therapy in that they may display the long term dimensional stability and patency of native arteries and vessels with normal physiologic functionality.

Historically, the seeding and culturing of vascular grafts, and tissue in general, has taken place in a static environment such as a Petri or culture dish. However, there are disadvantages to seeding and culturing tissue in such an environment. For example, the lack of circulation of nutrients in these static systems results in a slow and ineffective seeding and culturing process. Moreover, cells which are seeded and cultured in a dynamic environment are more likely to tolerate the physiological conditions which exist in the human body once implanted. Thus, there exists a need for a dynamic environment in which to seed and culture tissue engineered vascular grafts and other prosthetic devices.

SUMMARY OF THE INVENTION

It is therefore an object of the invention to provide a dynamic environment for seeding, culturing, and testing vascular grafts of any desired length or diameter.

It is a further object of the invention to provide a precise mechanical device with a minimum of moving parts to provide such an environment.

It is yet a further object of the invention to provide a closed system free from contamination for sterilizing, seeding, culturing, storing, shipping, and testing vascular grafts.

In accordance with the present invention, there is provided an apparatus and method for sterilizing, seeding, culturing, storing, shipping, and testing vascular grafts. Specifically, the present invention is an apparatus and method for seeding and culturing vascular grafts with human cells, resulting in a tissue engineered vascular graft populated with viable human cells.

The apparatus according to the invention comprises a fluid reservoir, a pump, at least one graft treatment chamber (treatment chamber), a tube for supporting the graft in the treatment chamber, and an alternating pressure source for applying a radial stress to the prosthesis housed in the treatment chamber. In an alternative embodiment the apparatus according to the invention provides a means for attaching at least one vascular graft directly in-line with the fluid reservoir. The alternating pressure source forces fluid through the vascular graft subjecting it to radial and shear stresses.

Applying shear and/or radial stresses to the vascular graft during seeding and culturing simulates physiological conditions. This is believed to produce a prosthesis that is more likely to tolerate the physiological conditions found in the human body. In this manner, the invention advantageously utilizes a mechanically non-complex apparatus to create a dynamic environment in which to seed and culture tissue engineered vascular grafts or other implantable devices.

BRIEF DESCRIPTION OF THE DRAWINGS

These and other features, aspects, and advantages of the present invention will become more readily apparent from the following detailed description, which should be read in conjunction with the accompanying drawings in which.

DETAILED DESCRIPTION OF THE INVENTION

Figure 1:
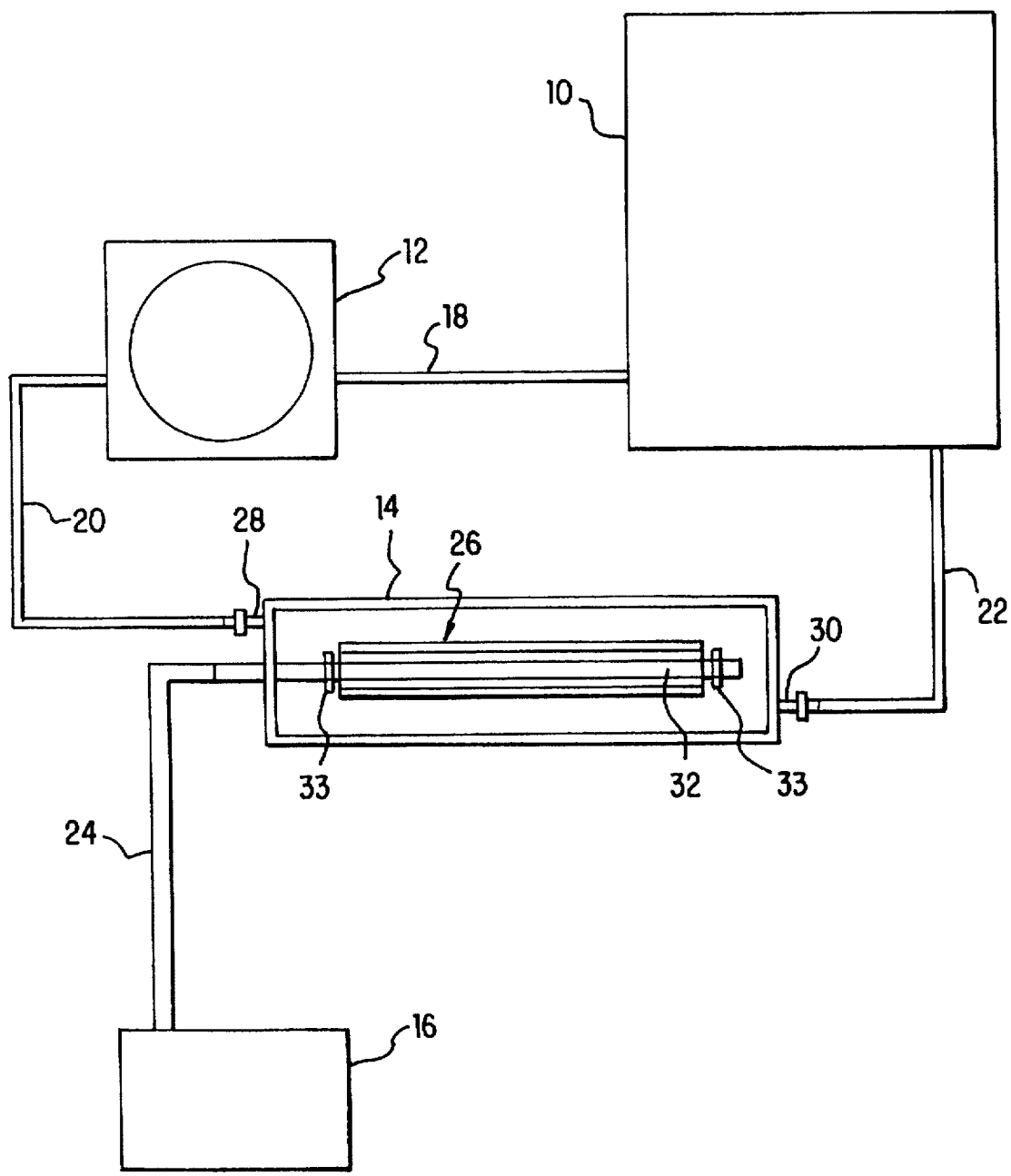
FIG. 1 is a schematic diagram illustrating an apparatus according to the present invention for sterilizing, seeding, culturing, storing, shipping, and testing a prosthesis.

The following embodiments of the present invention will be described in the context of an apparatus and method for sterilizing, seeding, culturing, storing, shipping, and testing vascular grafts, although those skilled in the art will recognize that the disclosed methods and structures are readily adaptable for broader application. Note that whenever the same reference numeral is repeated with respect to different figures, it refers to the corresponding structure in each such figure.

FIG. 1 discloses a system for sterilizing, seeding, culturing, storing, shipping, and testing vascular grafts. According to a preferred embodiment of the invention, this system primarily comprises a fluid reservoir 10, a pump 12, a treatment chamber 14, and an alternating pressure source 16.

Fluid reservoir 10 is used to store fluid for the system. Two illustrative suitable reservoirs are the Gibco-BRL 1L media bag and any rigid container capable of sterilization. Reservoir 10 may include a one way filter so as to provide a direct source of gas to the fluid within the system. Examples of fluid which may be used in the system include, but are not limited to, sterilizing fluid, tanning fluid, fluid containing cells, or fluid containing a culture medium. It is to be understood that during testing, seeding, and culturing in a preferred embodiment, the fluid may be advantageously kept at human body temperature, and may be composed of a fluid which approximates the viscosity of human blood. One illustrative example of a solution which approximates the viscosity of blood is saline with glycerol.

The fluid contained in reservoir 10 is retrieved through fluid line 18 by pump 12. Fluid line 18, as well as all other fluid lines in the system, may be made of any type of medical grade, durable tubing suitable for transporting the fluid in use. Pump 12 may be any fluid pump which can achieve variable flow rates. One such pump is the Masterflex L/S Digital Drive peristaltic pump manufactured by Cole-Palmer, although one skilled in the art could select from a variety of commercially available pumps. Pump 12 propels the fluid from reservoir 10 to treatment chamber 14 through fluid line 20.

Treatment chamber 14 preferably may be composed of any biocompatible, rigid material capable of being sterilized such as Teflon, polycarbonate, PVC, or stainless steel. However, it could also be made of a flexible material that could aid in the control of fluid volume surrounding the vascular grafts during culture or cryopreservation. Treatment chamber 14 may be comprised of two sections which are secured and made leak proof through any standard means such as inner and outer threads or the use of bonding agents. In order to view vascular grafts within treatment chamber 14, a viewing port may be placed at any point on the chamber, or alternatively, the chamber may be made of an optically clear material such as polycarbonate or PVC.

Inlet port 28 and outlet port 30 of treatment chamber 14 allow for the perfusion and/or circulation of fluid into and through the chamber. Inlet port 28 and outlet port 30 are also used to attach treatment chamber 14 to fluid lines 20 and 22 respectively. Fluid line 22 connects chamber 14 back to fluid reservoir 10 so as to create a closed system.

Treatment chamber 14 houses an expandable tube 32 upon which may be placed a vascular graft scaffolding 26. As discussed in detail in both of the patents incorporated by reference below, scaffolding 26 may illustratively consist of any knitted, braided, woven, felted, or synthesized materials that are bioresorbable and/or biocompatible, as well as any native graft scaffolding material. Tube 32 may be comprised of any suitable elastomeric material, such as PET or silicone angioplasty balloons, which is capable of expanding and contracting. Treatment Chamber 14 and tube 32 may be made any length or diameter so as to hold a vascular graft scaffolding 26 of any length or diameter. This is advantageous, as the system may be used to sterilize, seed, culture, store, ship, and test vascular grafts of any size, such as coronary, carotid, iliac, and peripheral leg grafts. A porous clip or grommet 33 may be placed on tube 32 at both ends of scaffolding 26 to hold the scaffolding firmly in place on the tube during treatment. However, one skilled in the art will understand that any structure that allows for retention of the scaffolding 26 on tube 32 may be used. Grommets 33 are beneficial, as the tubing can be made smaller than the grafts so as to allow for the perfusion and/or circulation of fluids in between the graft and the tube, without the possibility of slippage of the graft on the tube.

Figure 2:
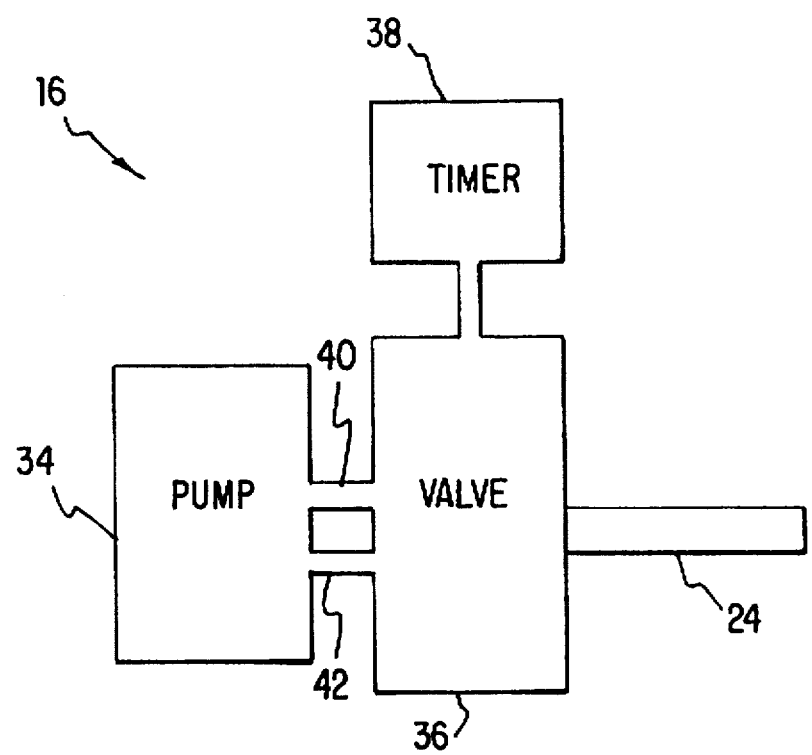
FIG. 2 is a block diagram illustrating a preferred embodiment of an alternating pressure source.

Tube 32 may be expanded and contracted by alternating pressure source 16, a preferred embodiment is shown in detail in FIG. 2. Specifically, FIG. 2 shows pump 34 which may be any standard pump capable of providing both positive pressure and negative (or vacuum) pressure, such as a piston or diaphragm pump. Valve 36 accepts the positive pressure and negative pressure from pump 34 through lines 40 and 42 respectively. Due to signals from timer 38, valve 36 causes alternating pressure to be applied to tube 32 from line 24. Valve 36 may be any type of in-line valve capable of directing and regulating multiple pressure lines. One such valve is the MAC 45S, model 45A-AA1-DAAA-1BA.

By expanding and contracting tube 32 with alternating pressure source 16, tube 32 places a varying radial stress on vascular graft scaffolding 26 simulating physiological conditions. This may produce a prosthesis that is more likely to tolerate physiological conditions found in the body.

Figure 3:
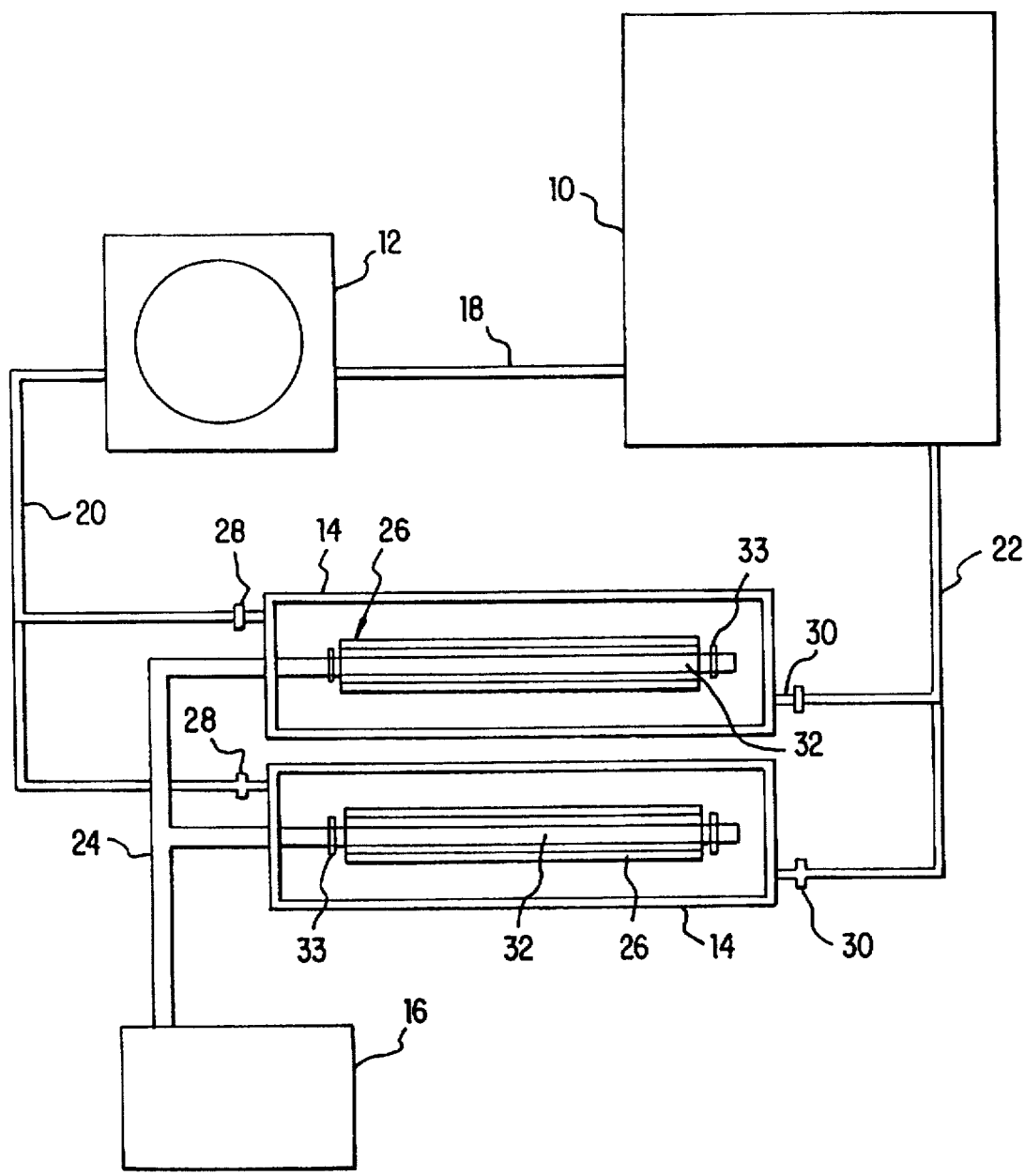
FIG. 3 is a schematic diagram illustrating an alternative exemplary embodiment of the present invention for sterilizing, seeding, culturing, storing, shipping, and testing a prosthesis, in which a plurality of prostheses may be treated simultaneously.

The system according to the present invention may contain a plurality of chambers 14 for treating a plurality of vascular grafts. FIG. 3 discloses a system according to the present invention which contains two treatment chambers 14. Although FIG. 3 illustrates the connection of only two treatment chambers to the system, it will be apparent to one skilled in the art that any number of chambers may be connected to the system in similar fashion. Specifically, line 20 may be split to connect to each inlet 28, line 24 may be split to connect to each tube 32, and line 22 may be split to connect to each outlet 30 of each chamber 14 in the system. In this manner, a plurality of vascular grafts may be simultaneously seeded, cultured, or tested.

Alternatively, each treatment chamber 14 may be connected to a separate reservoir 10 and pump 12 so that multiple treatment chambers in a system would only share a single alternating pressure source 16. It is to be understood that pump 12 with multiple pump lines may also be used so that each treatment chamber 14 in the system would use the same alternating pressure source and same pump 12 (each using a different pump line), but would be connected to a different media reservoir 10.

Figure 4:
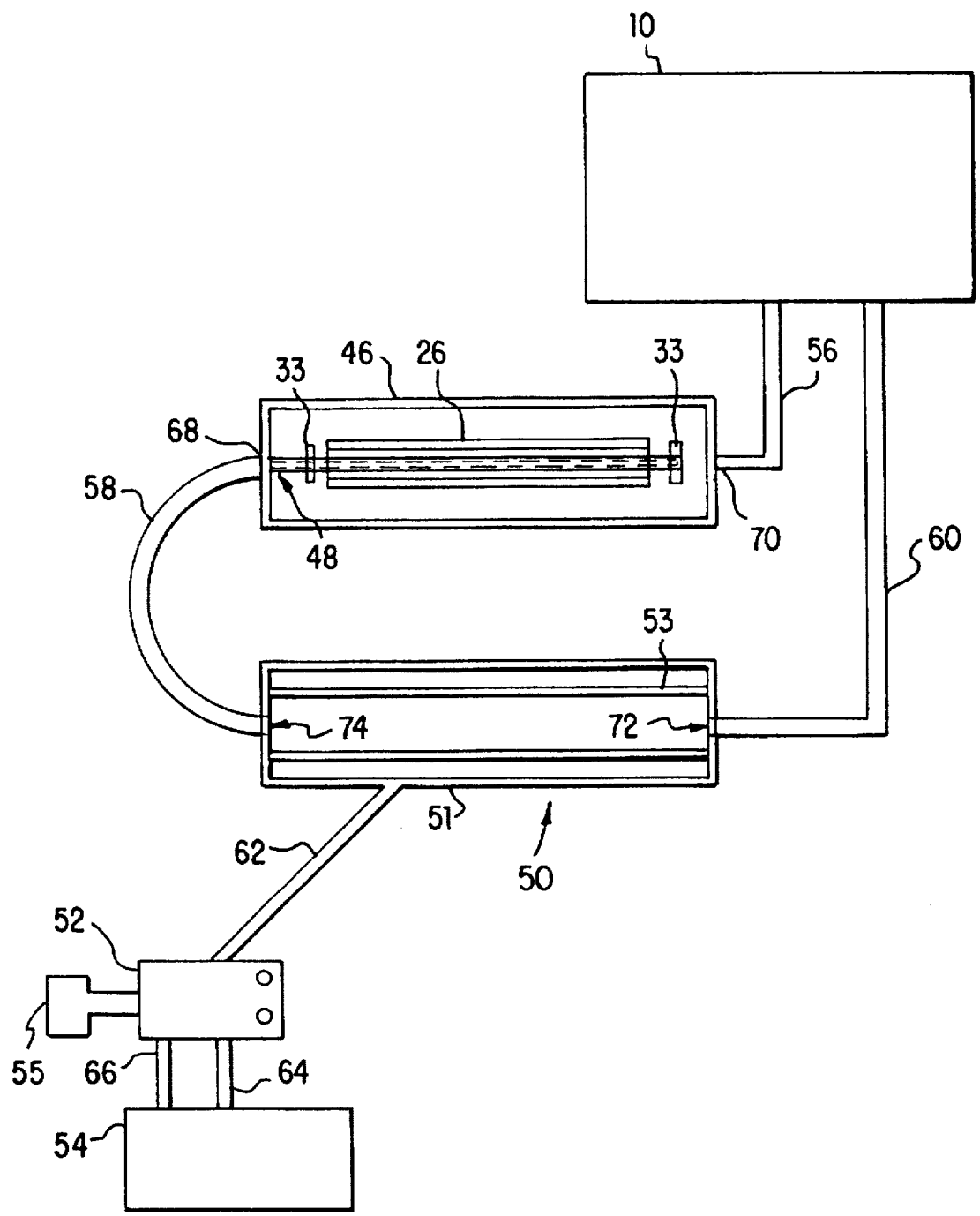
FIG. 4 is a schematic diagram illustrating another alternative exemplary embodiment of an apparatus according to the present invention for sterilizing, seeding, culturing, storing, shipping, and testing a prosthesis.

FIG. 4 discloses an alternative embodiment of the invention for sterilizing, seeding, culturing, storing, shipping, and testing vascular grafts. According to this embodiment of the invention, the system primarily comprises a fluid reservoir 10, a bladder pump 50, a treatment chamber 46, and an alternating pressure source 54.

Fluid reservoir 10 and the fluids which it may contain are described in detail in conjunction with FIG. 1.

Treatment chamber 46 may be composed of any biocompatible, rigid material capable of being sterilized such as Teflon, polycarbonate, PVC, or stainless steel. Treatment chamber 46 may be comprised of two sections which are secured and made leak proof through any standard means such as inner and outer threads or the use of bonding agents. In order to view vascular grafts within treatment chamber 46, a viewing port may be placed at any point on the chamber, or alternatively, the chamber may be made of an optically clear material such as polycarbonate or PVC.

Treatment chamber 46 houses porous tube 48 upon which may be placed vascular graft scaffolding 26. Scaffolding 26 is discussed in detail in conjunction with FIG. 1. Porous tube 48 may be comprised of any suitable rigid material, such as Teflon, PVC, polycarbonate, or stainless steel, which may be made fluid permeable. One illustrative example of a suitable porous tubing is the porous plastic tubing manufactured by Porex Technologies. Alternatively, porous tube 48 may be comprised of any suitable elastomeric material, such as PET or angioplasty balloons, that is capable of expanding and contracting, and that may be made fluid permeable. Treatment Chamber 46 and tube 48 may both be made any length or diameter so as to hold vascular graft scaffolding 26 of any length or diameter. This is advantageous, as the system may be used to sterilize, seed, culture, store, ship, and test vascular grafts of any size. Porous clips or grommets 33 may be placed on tube 48 at both ends of scaffolding 26 to hold the scaffolding in place on the tube during treatment.

Inlet port 68 and outlet port 70 of treatment chamber 46 allow for the perfusion and/or circulation of fluid into and through the chamber. Inlet port and outlet port 70 are also used to attach treatment chamber 46 to fluid lines 58 and 56 respectively. Fluid line 56 connects chamber 46 back to fluid reservoir 10 so as to create a closed system. It is to be understood that although only one treatment chamber 46 is shown in FIG. 4, fluid lines 56, 58, and 60 may be branched so as to connect more than one treatment chamber in parallel to the system.

The fluid contained in reservoir 10 is retrieved through fluid line 60 by bladder pump 50. Fluid line 60, as well as all other fluid lines in the system, may be made of any type of medical grade, durable tubing suitable for transporting the fluid in use. Bladder pump 50 is comprised of a pneumatic pressure chamber 51 and a bladder 53, which may be comprised of a suitable elastomeric material. An illustrative suitable bladder is the Cutter/Miles double valved hand activated blood pump. Bladder pump 50 forces fluid from reservoir 10 to treatment chamber 46 through fluid line 58 by being alternately compressed and expanded by alternating pressure source 54 in conjunction with valve 52 and timer 55. Alternating pressure source 54 preferably may be any standard pump capable of providing positive and negative (or vacuum) pressure, such as a piston or diaphragm pump. Valve 52 accepts the positive pressure and negative pressure from pump 54 through lines 64 and 66, respectively. Due to signals from timer 55, valve 52 causes alternating positive and negative pressure to be applied to bladder 53 from line 62. Valve 52 may be any type of in-line valve capable of directing and regulating multiple lines. One such valve is the MAC 45S, model 45A-AA1-DAAA-1BA.

When negative pressure is applied to bladder 53, fluid will be drawn from fluid reservoir 10 through fluid line 60 until bladder 53 is filled with fluid and is in an expanded state. During expansion of bladder 53, check valve 74 will ensure that no fluid is drawn from fluid line 58. Once the signal from timer 55 causes a positive pressure to be applied to bladder 53, the fluid contained in the bladder is forced out of the bladder and through fluid line 58 to treatment chamber 46. When fluid is forced out of bladder 53, check valve 72 will ensure that no fluid is forced back into fluid line 60. This causes, a pulsitile, cyclic fluid flow to treatment chamber 46 through tube 48 and out of port 70.

If tube 48 is comprised of a rigid porous material, then the varying fluid pressure caused by the action of bladder pump 50 will force fluid to flow through the porous material. The fluid flow through the porous material will place a varying radial stress on vascular graft scaffolding 26. Alternatively, if tube 48 is comprised of a porous elastomeric material, tube 48 may be expanded and contracted by the varying fluid pressure provided by bladder pump 50. By expanding and contracting porous tube 48 with bladder pump 50, tube 48 places a varying radial stress on vascular graft scaffolding 26. Moreover, as is the case with a rigid tube 48, the fluid flow through the elastomeric porous material will also place a varying radial stress on scaffolding 26. This places a cyclical radial stress on the scaffolding and cells supported thereon. This produces vascular grafts that are more likely to tolerate the physiological conditions found in the human body.

Figure 5:
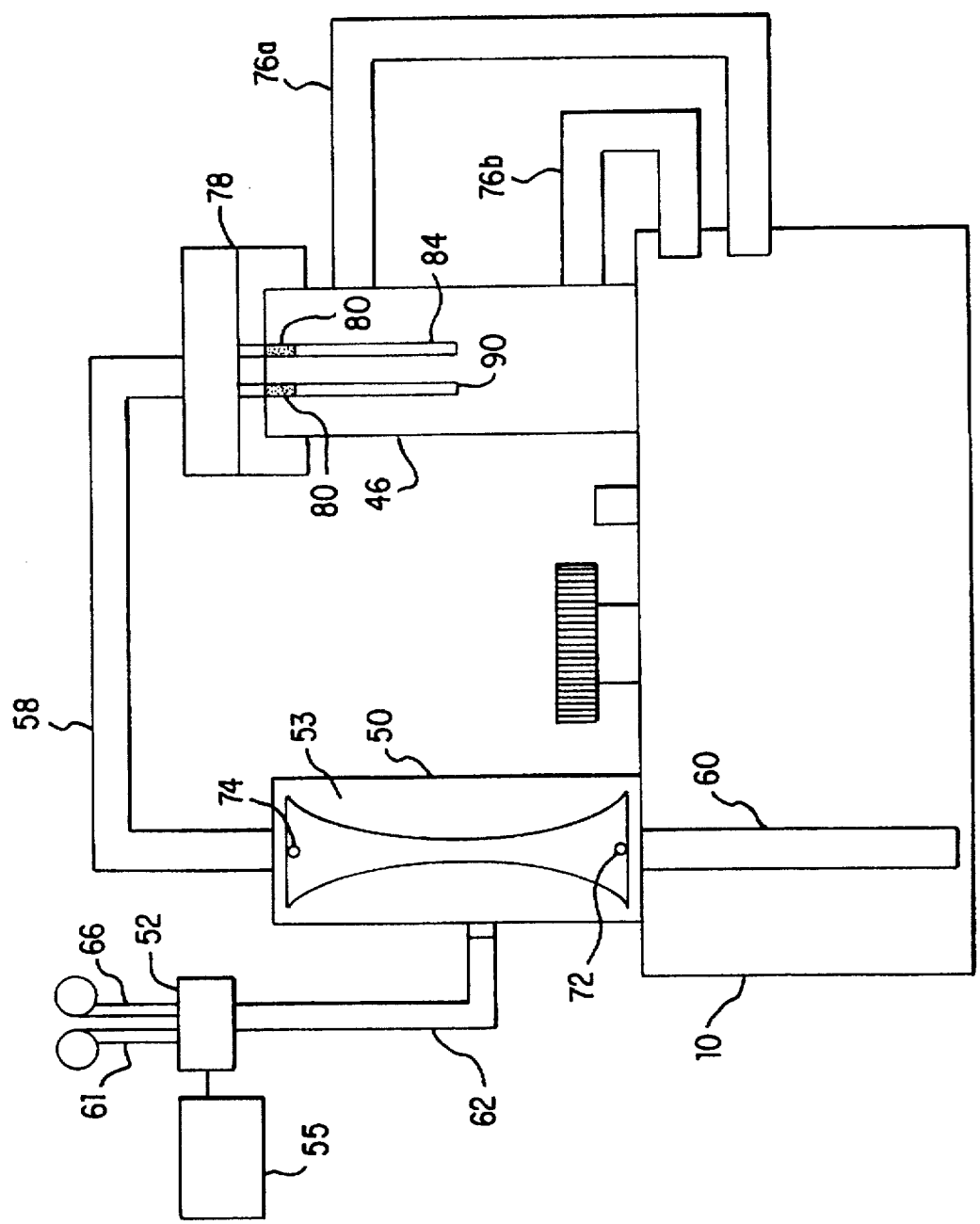
FIG. 5 is a schematic diagram illustrating yet another alternative exemplary embodiment of an apparatus according to the present invention for sterilizing, seeding, culturing, storing, shipping, and testing a prosthesis.
Figure 6:
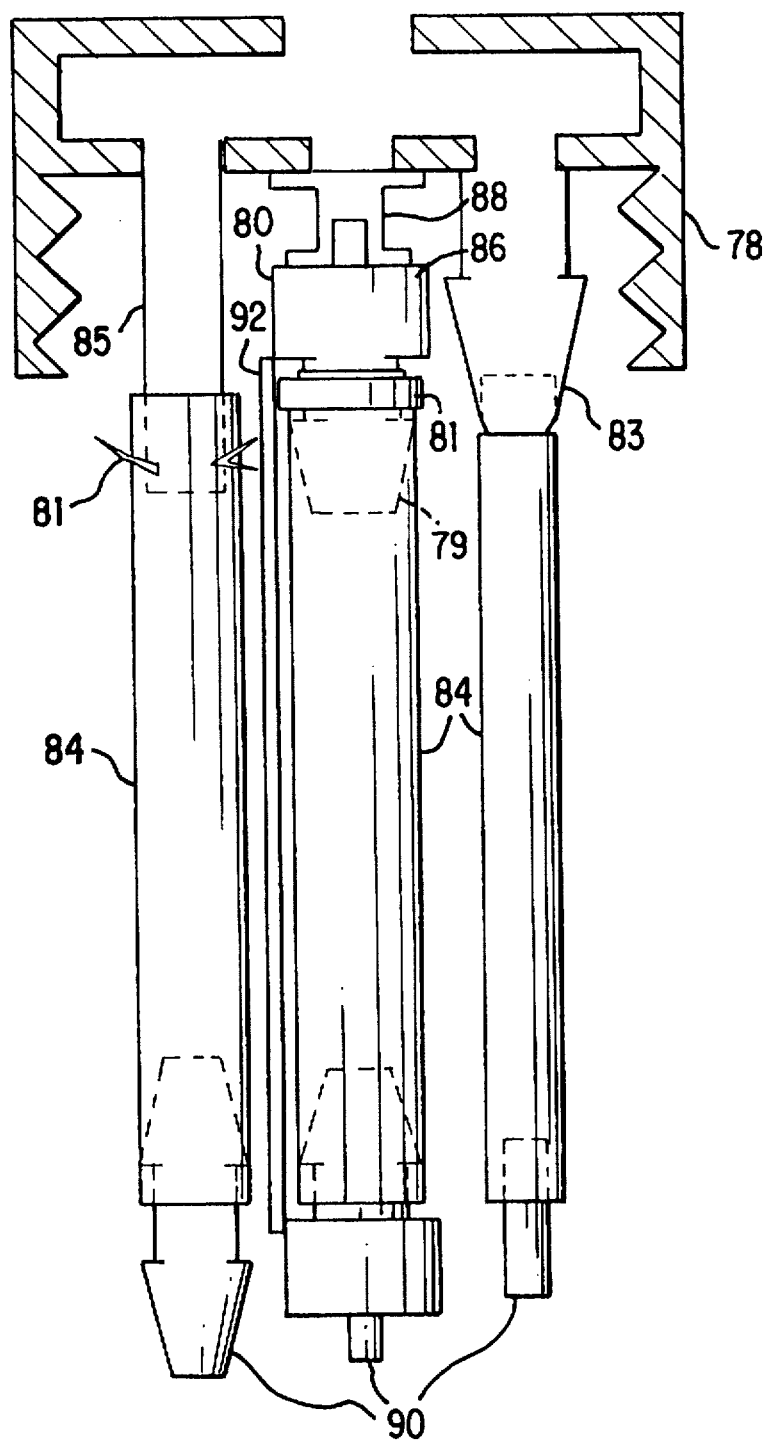
FIG. 6 is a schematic diagram illustrating some preferred alternatives for fluidly connecting a vascular graft within the present invention for sterilizing, seeding, culturing, storing, shipping, and testing a prosthesis.

FIG. 5 illustrates a further alternative embodiment of the present invention. The bioreactor housing material and construction is described in detail in conjunction with FIG. 4; except as noted below. In this embodiment vascular graft 84 is connected directly to treatment chamber cap 78 using luer 80 or other appropriate connecting means. The connecting means provides a means for the fluid to enter vascular graft 84 from fluid line 58. Treatment chamber cap 78 provides a means for evenly diffusing fluid to multiple vascular grafts undergoing treatment within treatment chamber 46. As best shown in FIG. 6 luer barb 80 is placed inside the vascular graft material and vascular graft 84 is secured by any conventional means for attaching 81 such as suture, c-clips, surgical staples, medical grade bonding agents, tie wraps, or elastomeric bands. Alternatively, vascular graft 84 could be placed within a larger diameter luer 83 and secured by compressing vascular graft 84 against the inner wall of luer 83. Another alternative is to place vascular graft 84 over mandrel 85 and secure it in a similar fashion. Luer 80 or mandrel 85 may be comprised of a slightly porous material to allow for tissue ingrowth at the attachment site. Once secured to the connecting means, the opposite end of the connecting means is then fluidly connected to the inside of treatment chamber cap 78. As by example, vascular graft 84 is connected to barbed end 79 of male luer 80 as described. Male end 86 of luer 80 is then attached to a complementing female end 88 which is attached to, or an integral part of treatment chamber cap 78. Another luer 90 or other restrictive orifice may be secured to the opposite end of vascular graft 84 to provide a back pressure during fluid circulation. The back pressure will place an increased varying radial stress on vascular graft 84 in response to the pulsitile flow. Fluid passing through vascular graft 84 may cause vascular graft 84 to undulate. A support member such as rod 92 may be attached by any conventional means to luer and to the opposite end of vascular graft 84 to suppress the undulations. Alternatively, the support member could extend from lower fitting 90 to the bottom or side of the housing. Passing the fluid directly through vascular graft 84, as opposed to through a flexible tube within the graft as in previously described embodiment of the invention, subjects the inside wall of the graft to shear stress from impinging flow. Applying shear and/or radial stresses to vascular graft 84 during seeding and culturing simulates physiological conditions.

A person skilled in the art will recognize that multiple ends of a branched (e.g. y-shaped) vascular graft may be attached to treatment chamber cap 78 as described by securing the separate arms of the branches to multiple fittings 80. Therefore, the instant invention enables one skilled in the art to seed culture or treat single branch or multibranched vascular grafts. Also, the vertical orientation of the grafts shown in FIG. 5 is not necessary if the graft is supported by an internal support structure which does not unduly obstruct flow impingement on interior surfaces of the grafts which create shear stresses. Such support structures could include a splint structure or rigid tubular screens with large, unobstructing openings.

After vascular graft 84 is attached to treatment chamber cap 78, it is housed in treatment chamber 46. Treatment chamber 46 can be secured to treatment chamber cap 78 by any conventional means for securing such as threaded screws, clamping against a set of ferrules or flanges and made leak-proof by the use of a gasket or o-ring. Additionally, vascular graft 84 can be removed from treatment chamber 46 and placed into an alternative vascular graft housing designed for cryopreservation, shipping, or storage.

Fluid is drawn from base reservoir 10 via fluid line 60 into bladder pump 50, and transferred to treatment chamber 46 through fluid line 58 as described in detail in conjunction with FIG. 4. Since vascular graft 84 is in-line with fluid line 58 fluid will pass directly through vascular graft 84 when entering treatment chamber 46. Two fluid lines 76a, and 76b connect treatment chamber 46 to base reservoir 10 so as to create a closed system.

In a preferred mode of operation, fluid lines 76a, and 76b are alternately closed during the seeding and growth of vascular graft 84. During seeding it is preferred to maintain vascular graft 84 suspended above the fluid. In this mode fluid line 76a is closed, and 76b is open thereby allowing fluid to flow back to reservoir 10 through fluid line 76b and partially or substantially emptying treatment chamber 46 of fluid. During growth, it is preferred to maintain vascular graft 84 submerged in fluid. In this mode fluid line 76b is closed, and 76a is open thereby allowing the fluid to return to reservoir 10 through fluid line 76a substantially submerging vascular graft 84. A valve or clamp can be used to alternately open and close fluid lines 76a and 76b. One skilled in the art will recognize that electric, pneumatic or other automated valves controlled by a timing mechanism will also suffice to alternately open and close fluid lines 76a and 76b as described above.

It is to be understood that the inlet port and outlet port of treatment chamber 14 (in FIGS. 1 and 3) and treatment chamber 46 (in FIGS. 4 and 5) may be sealed in a known manner (e.g., luer locks or threaded plugs) so as to create a sealed treatment chamber free from contamination. The sealed chambers may be used to sterilize, store, and ship vascular grafts or other protheses. In particular, prior to placing a sealed chamber into the systems of FIGS. 1, 3, 4 and 5, vascular graft scaffolding 26 which is secured within sealed chambers 14 or 46 or vascular graft 84 which is secured within sealed chamber 46, may be sterilized by some chemical means such as ethylene oxide or peracetic acid, radiation means such as an electron beam or gamma rays, or by steam sterilization. Sealed treatment chambers 14 or 46, containing the sterilized vascular graft scaffolding, or the sterilized vascular graft may then be placed back into the systems of FIGS. 1, 3, 4 or 5 for seeding and culturing and unsealed without contaminating the system or the vascular graft.

Seeding and culturing of the vascular graft in treatment chambers 14 and 46 is generally accomplished by known techniques, with the added benefits and advantages gained from the radial and/or shear stresses placed upon the vascular graft during growth. Examples of suitable seeding and culturing methods for the growth of three-dimensional cell cultures are disclosed in U.S. Pat. No. 5,266,480, which is incorporated herein by reference. The techniques described in U.S. Pat. No. 5,266,480 for establishing a three-dimensional matrix, inoculating the matrix with the desired cells, and maintaining the culture may also be readily adapted by a person of ordinary skill in the art for use with the present invention.

Once the vascular graft has reached the desired level of cell density, a preservative may then be pumped into treatment chamber 14 or 46. Once the treatment chambers are filled with the preservative, the inlet ports and outlet ports of the chambers may be closed, again creating a sealed chamber which may then be used to store and/or ship the cultured and preserved vascular graft. Preferably, the preservative is a cryo-preservative so that the graft may be frozen in chamber 14 or 46. In this manner, sealed treatment chamber 14 or 46 may be used to sterilize, culture, store, and ship vascular grafts or other protheses.

Various embodiments of the invention have been described. The descriptions are intended to be illustrative, not limitative. Thus, it will be apparent to those skilled in the art that modifications may be made to the invention as described without departing from the scope of the claims set out below.

We claim:

1. An apparatus, comprising:
    at least one vascular graft designed to facilitate three-dimensional tissue growth on said graft, said graft comprising a biocompatible, non-living three-dimensional framework having interstitial spaces bridgeable by cell;
    a chamber having a first port and a second port for flow of fluid therethrough;
    a means for connecting said at least one vascular graft within said chamber; and
    a means for imparting radial and shear stresses to said at least one vascular graft.

2. The apparatus of claim 1, wherein said imparting means is attached to said connecting means such that fluid may pass through said at least one vascular graft.

3. The apparatus of claim 2, wherein said imparting means comprises a means for forcing fluid through said at least one vascular graft such that fluid comes into contact with said at least one vascular graft; and said means for forcing fluid comprises a means for alternating the flow of said fluid.

4. The apparatus of claim 3, wherein said imparting means further comprises a means for creating an alternating back pressure within said at least one vascular graft.

5. The apparatus of claim 4, wherein said means for creating back pressure comprises a means for restricting the flow of said fluid out of said at least one vascular graft.

6. The apparatus of claim 5, wherein said means for alternating the flow of said fluid comprises a pump.

7. An apparatus for seeding and culturing vascular grafts, comprising:
    at least one vascular graft designed to facilitate three-dimensional tissue growth on said graft, said graft comprising a biocompatible, non-living three-dimensional framework having interstitial spaces bridgeable by cells;
    a housing defining a seeding and culturing chamber with a first and at least two second ports to permit flow of a medium therethrough; and
    a means for connecting said at least one vascular graft within said chamber, said connecting means fluidly connecting said at least one vascular graft to said first port such that medium flows from said first port through said at least one vascular graft and out at least one of said second ports; and wherein said flow of medium through said at least one vascular graft applies radial and shear stresses to said at least one vascular graft.

8. The apparatus of claim 7, further comprising a pump for providing an alternating flow of said medium to said housing.

9. The apparatus of claim 7, wherein said at least one vascular graft hangs downward in a generally vertical orientation within said housing.

10. The apparatus of claim 7, wherein said flow comes into contact with said at least one vascular graft imparting radial and shear stresses thereto.

11. An apparatus for seeding and culturing vascular grafts, comprising:

a chamber defined by top and bottom walls and at least one side wall;

at least one fluid inlet to said chamber and at least one fluid outlet from said chamber;

a vascular graft designed to facilitate three-dimensional tissue growth on said graft, said graft comprising a biocompatible non-living three-dimensional having interstitial spaces bridgeable by cells:

at least one fitting mounted within the chamber, in fluid communication with the inlet, said fitting being configured and dimensioned to receive and hold open an end of said vascular graft to permit flow of fluid through said graft; and a fluid supply system communicating with the fluid inlet to provide pulsatile fluid flow through said at least one fitting.

12. The apparatus according to claim 11, wherein said at least one fitting is mounted on the top wall of the chamber such that a vascular graft received thereon hangs downward in a generally vertical orientation.

13. The apparatus according to claim 12, wherein:

the chamber includes a first fluid outlet and at least a second fluid outlet disposed vertically above the first fluid outlet;

the first fluid outlet being positioned to provide a height of fluid in the chamber that is below a vascular graft received on the at least one fitting; and the at least one second outlet being positioned above the first outlet at a height sufficient to provide a fluid height within the chamber which substantially covers a vascular graft received on the at least one fitting.

14. The apparatus according to claim 13, wherein said outlets communicate with the fluid supply system to provide a closed fluid supply system.

15. The apparatus according to claim 11, further comprising at least one second fitting configured and dimensioned to be connected to an end of the tubular vascular graft opposite said fitting mounted within the chamber, said at least one second fitting defining an orifice having a diameter less than the tubular vascular graft inner diameter.

16. The apparatus according to claim 11, wherein the top wall comprises a manifold with at least one fluid inlet and a plurality of fittings for receiving a plurality of tubular vascular grafts, said manifold distributing fluid substantially equally to each of said fittings.

17. A method for seeding and culturing a vascular graft, comprising:

providing a vascular graft designed to facilitate three-dimensional tissue growth on said graft, said graft comprising a biocompatible, non-living three-dimensional framework having interstitial spaces bridgeable by cells:

exposing said vascular graft to a fluid media; and imparting radial and shear stresses to said vascular graft during at least one of said seeding or culturing to simulate physiological conditions.

18. The method of claim 17, wherein:

said exposing step comprises, directing a fluid flow through said vascular graft; and said imparting step comprises, forcing said fluid media through said vascular graft with a pulsitile flow such that radial and shear stresses are imparted to said vascular graft.

19. The method of claim 18, wherein said exposing step further comprises:

supporting an end of the vascular graft with the hollow member such that the graft hangs in a generally vertical orientation; and securing said vascular graft to said hollow member.

20. The method of claim 19, wherein:

said step of supporting comprises, placing said vascular graft inside the hollow member; and said step of securing comprises compressing said vascular graft against the inside wall of the hollow member.

21. The method of claim 19, wherein:

said step of supporting comprises, placing said vascular graft over the hollow member; and said step of securing comprises compressing said vascular graft against the outside wall of said hollow member.

22. A method for treating a vascular graft comprising:

providing a vascular graft designed to facilitate three-dimensional tissue growth on said graft, said graft comprising a biocompatible, non-living three-dimensional framework having interstitial spaces bridgeable by cells; providing a fluid media source; and pumping said fluid media from said source to create a fluid stream;

fluidly connecting said vascular graft with said fluid stream within a media chamber; and variably moving said vascular graft between an expanded position and an un-expanded position by directing said flow through the graft.

23. The method of claim 22, wherein:

said step of fluidly connecting comprises, placing said vascular graft over a hollow member, and securing said vascular graft to said hollow member by compressing said vascular graft against the outside wall of said hollow member; and said step of variably moving comprises varying said media stream through said vascular graft such as to impart varying pressures within said vascular graft.

24. The method of claim 22, wherein:

said step of fluidly connecting comprises, placing said vascular graft inside a hollow member by compressing said vascular graft against the inside wall of said hollow member; and securing said vascular graft to said hollow member, and said step of variably moving comprises, varying said media stream through said vascular graft such as to impart varying pressures within said vascular graft.

25. An apparatus, comprising:

a tubular prosthesis designed to facilitate three-dimensional tissue growth on said prosthesis, said prosthesis comprising a biocompatible, non-living three-dimensional framework having interstitial spaces bridgeable by cells;

a chamber having a first port and a second port for flow of fluid therethrough; a support structure located within said chamber configured and dimensioned to support the tubular prosthesis; and means for imparting a radial stress to the prosthesis mounted on said support structure.

26. The apparatus of claim 25 wherein said support structure is moveable between a first position and a second position.

27. The apparatus of claim 26 wherein said imparting means comprises means for moving said support structure between the first and second positions.

28. The apparatus of claim 27, wherein said support structure comprises an expandable tubular member having an outer diameter that is variable in response to pressure within the tubular member, said tubular member adapted to receive the tubular prosthesis thereover.

29. The apparatus of claim 28, wherein said moving means comprises an alternating pressure source communicating with the tubular member for moving said support structure from the first position to the second position.

30. The apparatus of claim 25, wherein said support structure is comprised of a porous material.

31. The apparatus of claim 30, wherein said imparting means comprises means for forcing fluid flow through said support structure.

32. The apparatus of claim 31, wherein said forcing means comprises a pump providing alternating pressure.

33. The apparatus of claim 25, further comprising a three-dimensional tissue, said tissue comprising a plurality of cells attached to and substantially enveloping said tubular prosthesis.

34. An apparatus, comprising:

a chamber having a first port and a second port for flow of fluid therethrough;

a variable support structure located within said chamber configured and dimensioned to support a tubular prosthesis;

said support structure being moveable between a first position and a second position, wherein movement of said support structure between said positions creates varying radial stresses in the prosthesis supported thereby.

35. The apparatus of claim 34, wherein the support structure comprises an expandable member that is adapted to receive the tubular prosthesis thereover.

36. The apparatus of claim 35, wherein the expandable member comprises an expandable tubular member having an outer diameter that is variable in response to pressure within the tubular member.

37. The apparatus of claim 36, wherein the expandable tubular member comprises an angioplasty balloon.

38. The apparatus of claim 36 further comprising an alternating pressure source communicating with the tubular member for moving said support structure from said first position to said second position.

39. The apparatus of claim 38, wherein said alternating pressure source comprises:

a pump for providing a first level of pressure and second level pressure;

a valve connected in between said pump and said support structure for alternatingly allowing the first level of pressure and the second level of pressure to be placed on said support structure, wherein the first level of pressure corresponds to the first position and the second level of pressure corresponds to the second position.

40. The apparatus of claim 39, wherein the valve is connected to a timer for variably opening and closing the valve.

41. The apparatus of claim 36, wherein the expandable tubular member is sized such that in at least the first position the tubular member and prosthesis are spaced apart to define a passage that permits fluid to circulate between said tubular member and said prosthesis.

42. The apparatus of claim 41, wherein said prosthesis is held in place on said support structure by a grommet.

43. The apparatus of claim 34, further comprising a tubular prosthesis supported by said support structure and designed to facilitate three-dimensional tissue growth on said prosthesis, said prosthesis comprising a biocompatible, non-living three-dimensional framework having interstitial spaces bridgeable by cells.

44. The apparatus of claim 43, further comprising a three-dimensional tissue, said tissue comprising a plurality of cells attached to and substantially enveloping said tubular prosthesis.

45. An apparatus for seeding and culturing vascular grafts, comprising:

a housing defining a seeding and culturing chamber with first and second ports to permit flow of a medium therethrough;

a vascular graft support structure mounted in the chamber, said structure adapted for supporting a vascular graft such that media flow between said ports is permitted to circulate around the surfaces of the graft; and a pressure source for alternatingly expanding said vascular graft support structure from a first position to a second position to apply a varying radial stress on the graft.

46. The apparatus of claim 45, wherein said vascular graft support structure comprises an elastic tube.

47. The apparatus of claim 46, wherein said pressure source comprises:

a pump for providing a first level of pressure and a second level of pressure;

a valve connected in between said pump and said support structure for alternatingly allowing the first level of pressure and the second level of pressure to be placed on said support structure, the first level of pressure forcing said support structure into the first position and the second level of pressure forcing said support structure into the second position.

48. The apparatus of claim 45, further comprising a plurality of said housings.

49. The apparatus of claim 45, wherein the first and second ports of said housing may be sealed for enclosing, sterilizing, storing, and shipping the vascular graft.

50. An apparatus for three-dimensional tissue growth, comprising:

a tubular prosthesis designed to facilitate three-dimensional tissue growth on said prosthesis, said prosthesis comprising a biocompatible, non-living three-dimensional framework having interstitial spaces bridgeable by cells;

a housing defining a seeding and culturing chamber with first and second ports to permit flow of a medium therethrough; and a porous support structure mounted in the chamber configured and dimensioned to support the tubular prosthesis, said support structure fluidly connected to the first port such that medium flows from the first port through said porous support structure and out the second port;

wherein the medium flow through said support structure applies a radial stress on the prosthesis mounted on said support structure.

51. The apparatus of claim 50, further comprising a pump for providing a medium flow to said housing with varying pressure.

52. The apparatus of claim 51, wherein said pump is a bladder pump.

53. The apparatus of claim 50, wherein said support structure comprises a rigid porous tube.

54. The apparatus of claim 50, wherein said support structure comprises an elastic porous tube.

55. The apparatus of claim 50, further comprising a three-dimensional tissue, said tissue comprising a plurality of cells attached to and substantially enveloping said tubular prosthesis.

56. A method for seeding and culturing a tubular prosthesis, comprising:

exposing a tubular prosthesis to a fluid media for seeding and culturing, said prosthesis comprising a biocompatible, non-living three-dimensional framework having interstitial spaces bridgeable by cells; and imparting a radial stress to the prosthesis during said seeding and culturing to encourage a desired alignment of cells on the prosthesis.

57. The method of claim 56, wherein said step of imparting radial stress comprises:

placing said prosthesis on a support structure; and moving said support structure between a first position and a second position so that the radial stress is imparted to the prosthesis.

58. The method of claim 57, wherein said support structure comprises an elastic tube.

59. The method of claim 58, wherein said step of expanding said support structure comprises moving said tube from the first to the second position by a pump, said pump alternatingly providing a first level and a second level of pressure.

60. The method of claim 56, wherein said step of imparting radial stress comprises:

placing said prosthesis on a porous support structure; and forcing the fluid media through the porous support structure so that radial stress is imparted to the prosthesis from the fluid media.

61. The method of claim 60, wherein the porous support structure comprises a rigid tubular member.

62. A method for treating a tubular prosthesis comprising:

providing a fluid media source;

pumping the fluid media from said source to create a fluid stream;

providing a tubular prosthesis designed to facilitate three-dimensional tissue growth on said prosthesis, said prosthesis comprising a biocompatible, non-living three-dimensional framework having interstitial spaces bridgeable by cells;

holding the prosthesis in a media chamber communicating with the fluid stream; and variably moving said prosthesis from a first contracted position to a second expanded position in said fluid stream.

63. The method of claim 62, wherein the diameter of said prosthesis is varied by said step of variably moving said prosthesis.

64. The method of claim 63, wherein said step of holding comprises placing the prosthesis over an elastic tube in the chamber and said step of variably moving comprises moving said tube from a first expanded position to a second contracted position.

65. The method of claim 64, wherein said step of moving said tube from said first expanded position to said second contracted position is accomplished through the use of a pump, said pump alternatingly providing a first and a second level of pressure to said tube.

66. The method of claim 63, wherein said step of holding comprises placing the prosthesis over a porous tube structure in the chamber and said step of variably moving comprises forcing the fluid media through said tube structure with varying pressure.

67. The method of claim 66, wherein said step of forcing the fluid media through said tube structure is accomplished through the use of a pump, said pump alternatingly providing a first and a second level of pressure to said tube structure.

* * * * *